(12) United States Patent
Yamagishi et al.

(10) Patent No.: US 6,730,212 B1
(45) Date of Patent: May 4, 2004

(54) SENSOR FOR CHEMICAL AND BIOLOGICAL MATERIALS

(75) Inventors: Frederick G. Yamagishi, Newbury Park, CA (US); Thomas B. Stanford, Jr., Port Hueneme, CA (US); Camille I. Van Ast, Newbury Park, CA (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 09/679,428

(22) Filed: Oct. 3, 2000

(51) Int. Cl.[7] ............................................. G01N 27/327
(52) U.S. Cl. ..................... 205/777.5; 204/403.01; 204/403.1; 204/403.11; 427/58
(58) Field of Search ............... 204/403.01, 403.04, 204/403.1–403.12, 403.14; 205/777.5; 427/58, 213.3, 213.34

(56) References Cited

U.S. PATENT DOCUMENTS

| | | |
|---|---|---|
| 4,019,367 A | 4/1977 | Norsworthy |
| 4,334,880 A | 6/1982 | Malmros |
| 4,444,892 A | 4/1984 | Malmros |
| 4,457,161 A | 7/1984 | Iwanaga et al. |
| 4,624,756 A | 11/1986 | Matsuda et al. |
| 4,674,320 A | 6/1987 | Hirschfeld |
| 4,699,804 A | 10/1987 | Miyata et al. |
| 4,721,601 A | 1/1988 | Wrighton et al. |
| 4,822,465 A | 4/1989 | Jones et al. |
| 4,907,441 A | 3/1990 | Shurmer |
| 4,977,658 A | 12/1990 | Awano et al. |
| 5,018,380 A | 5/1991 | Zupancic et al. |
| 5,086,286 A | 2/1992 | Yasukawa et al. |
| 5,122,237 A | 6/1992 | Kim et al. |
| 5,208,301 A | 5/1993 | Epstein et al. |
| 5,234,566 A | 8/1993 | Osman et al. |
| 5,312,762 A | 5/1994 | Guiseppi-Elie |
| 5,331,287 A | 7/1994 | Yamagishi et al. |
| 5,337,018 A | 8/1994 | Yamagishi |
| 5,372,785 A | 12/1994 | Johnson et al. |
| 5,407,699 A | 4/1995 | Myers |

(List continued on next page.)

FOREIGN PATENT DOCUMENTS

| | | |
|---|---|---|
| EP | 0 596 973 B1 | 12/1995 |
| GB | 2 225 008 | 5/1990 |
| GB | 2 237 291 | 5/1991 |
| JP | 58-176538 | 10/1983 |
| JP | 63-215960 | 9/1988 |
| JP | 03-089156 | 4/1991 |
| JP | 05-296960 | 11/1993 |
| WO | 95/32422 | 11/1995 |
| WO | 97/04464 | 2/1997 |
| WO | 98/19153 | 5/1998 |
| WO | 02/29378 A2 | 4/2002 |

OTHER PUBLICATIONS

Onoda et al, Synthetic Metals, 1995, 71, pp. 2255–2256.*
Verghese et al, Chemistry of Materials, 1996, 8, pp. 822–824.*

(List continued on next page.)

Primary Examiner—Kaj K. Olsen
(74) Attorney, Agent, or Firm—Ladas & Parry

(57) ABSTRACT

A sensor and method for detecting biological and chemical agents comprising metal interdigitized electrodes coated with hybrid polymer-based conducting film and an instrument for applying electrical voltage to the electrodes and registering the change in voltage. The hybrid film also comprises indicator biomolecules encapsulated within the film or attached to it. When these indicator biomolecules come in a contact with a biological and chemical agent, morphological changes occur in the film and electrical current flowing through the electrodes is modulated. The change in current indicates the presence of a biological and chemical agent and is registered.

83 Claims, 4 Drawing Sheets

U.S. PATENT DOCUMENTS

| | | | |
|---|---|---|---|
| 5,417,100 A | 5/1995 | Miller et al. | |
| 5,491,097 A | 2/1996 | Ribi et al. | |
| 5,520,852 A | 5/1996 | Ikkala et al. | |
| 5,536,473 A | 7/1996 | Monkman et al. | |
| 5,540,862 A | 7/1996 | Cao et al. | |
| 5,571,401 A | 11/1996 | Lewis et al. | |
| 5,607,573 A | 3/1997 | Miller et al. | |
| 5,624,605 A | 4/1997 | Cao et al. | |
| 5,625,139 A | 4/1997 | Stormbom | |
| 5,698,083 A | * 12/1997 | Glass | 204/403.03 |
| 5,756,879 A | 5/1998 | Yamagishi et al. | |
| 5,766,934 A | 6/1998 | Guiseppi-Elie | |
| 5,922,537 A | 7/1999 | Ewart et al. | |
| 5,928,609 A | 7/1999 | Gibson et al. | |

OTHER PUBLICATIONS

Akkara, J., et al., "Synthesis of Two–Dimensional Electrooptic Polymer Networks Through Biocatalysis," *Polymer Preprints*, vol. 34, No. 2, pp 759–760 (Aug. 1993).

Araujo, Y.C., et al., "Structure of Silane Films and Their Adhesion Properties," *Mat. Res. Soc. Symp. Proc.*, vol. 407, pp 325–330 (1996).

Arkles, B., "Silane Coupling Agent Chemistry," *Silicon Compounds: Register and Review*, 5th Ed., pp 59–64 (1991).

Bartlett, P., et al., "Conducting Polymer Gas Sensors, Part I: Fabrication and Characterization," *Sensors and Actuators*, vol. 19, pp 125–140 (1989).

Bartlett, P., et al., "Conducting Polymer Gas Sensors, Part III: Results for Four Different Polymers and Five Different Vapours," *Sensors and Actuators*, vol. 20, pp 287–292 (1989).

Brumlik, C.J., et al., "Template Synthesis of Metal Microtubules," *J. Am. Chem. Soc.*, vol. 113, pp 3174–3175 (1991).

Buehler, M.G., et al., "Gas Sensor Test Chip," *Proceedings of the 1996 IEEE International Conference on Microelectronic Test Structures*, vol. 9, pp 105–110 (Mar. 1996).

Charlesworth, J.M., et al., "Mechanistic Studies on the Interactions Between Poly(pyrrole) and Organic Vapors,", *J. Phys. Chem.*, vol. 97, pp 5418–5423 (1993).

Cui, C.X., et al., "Two helical conformations of polythiophene, polypyrrole, and their derivatives," *The Americal Physical Society, Physical Review B*, vol. 40, No. 14, pp 9661–9670 (Nov. 15, 1989).

Evans, P., et al., "Synthesis and gas sensing properties of poly[tetra(pyrrol–1–yl(silane]," *J. Mater. Chem.*, vol. 6, No. 3, pp 295–299 (1996).

Faverolle, F., et al., "Caractérisation de dëpôts adhërents de polypyrrole sur substrats de verre," *J. Chim. Phys.*, vol. 92, pp 943–946 (1995).

Feng, J., et al., "Conformation of polyaniline: effect of mechanical shaking and spin casting," *Synthetic Metals*, vol. 84, pp 131–132 (1997).

Fox, M.A., et al., "Covalent Attachment of Arenes to $SnO_2$—Semiconductor Electrodes," *Journal of the American Chemical Society*, vol. 102, No. 12, pp 4029–4036 (Jun. 4, 1980).

Habib, M.A., et al., "Silanized Polyaniline as an Electrochromic Material," *J. Electrochem. Soc.*, vol. 138, No. 6, pp 1692–1695 (Jun. 1991).

Hwang, L.S., et al., "A Polymer Humidity Sensor," *Synthetic Metals*, vol. 55, No. 57, pp 3671–3676 (1993).

Imisides, M.D., et al., "Microsensors based on conducting polymers," *Chemtech*, pp 19–25 (May 1996).

Krutovertsev, S.A., et al., "Polymer film–based sensors for ammonia detection," *Sensors and Actuators B*, vol. 7, pp 492–494 (1992).

Kupila, E.–L., et al., "The effect of silanization and poly(ethylene oxide) on the electropolymerization of pyrrole," *Synthetic Metals*, vol. 62, pp 55–59 (1994).

Kuwabata, S., et al., "Investigation of the gas–transport properties of polyaniline," *Journal of Membrane Science*, vol. 91, pp 1–12 (1994).

Liang, W., et al., "Gas Transport in Electronically Conductive Polymers," *Chem. Mater.*, vol. 3, pp 390–391 (1991).

MacDiarmid, A.G., et al., "Secondary doping in polyaniline," *Synthetic Metals*, vol. 69, pp 85–92 (1995).

MacDiarmid, A.G., et al., "Thin films of Conjugated Polymers: Application in Sensors for Hydrocarbon Vapors, Microcontact–Printed Liquid Crystal Displays and Light Emitting Devices," *Polymer Preprints*, vol. 38, No. 1, pp 333–334 (Apr. 1997).

McGill, R.A., et al., "Surface and Interfacial Properties of Surface Acoustic Wave Gas Sensors," *Interfacial Design and Chemical Sensing*, pp 280–294 (1994).

McGovern, M.E., et al., "Role of Solvent on the Silanization of Glass with Octadecyltrichlorosilane," *Langmuir*, vol. 10, No. 10, pp 3607–3614 (1994).

Nishizawa, M., et al., "Electrochemical Preparation of Ultrathin Polypyrrole Film at Microarray Electrodes," *J. Phys. Chem.*, vol. 95, pp 9042–9044 (1991).

Nishizawa, M., et al., "Surface Pretreatment for Electrochemical Fabrication of Ultrathin Patterned Conducting Polymers," *J. Electrochem. Soc.*, vol. 140, No. 6, pp 1650–1655 (1993).

Nishizawa, M., et al., "Ultrathin polypyrrole formed at a twin–microband electrode in the presence of dodecylsulfate," *Journal of Electroanalytical Chemistry*, vol. 371, pp 273–275 (1994).

Oyama, N., et al., *Shinsozai*, vol. 4, pp 56–63 (1993).

Pandey, P.C., et al., "Acetylthiocholine/acetylcholine and thiocholine/choline electrochemical biosensors/sensors based on an organically modified sol–gel glass enzyme reactor and graphite paste electrode," *Sensors and Actuators B*, vol. 62, pp 109–116 (2000).

Partridge, A.C., et al., "High Sensitivity Conducting Polymer Sensors," *Analyst*, vol. 121, pp 1349–1353 (Sep. 1996).

Paschen, S., et al., "Morphology of a conducting polymer and its relation to the electronic properties," *Acta Polymer*, vol. 47, pp 511–519 (1996).

Paul, E.W., et al., "Resistance of Polyaniline Films as a Function of Electrochemical Potential and the Fabrication of Polyaniline–Based Microelectronic Devices," *J. Phys. Chem.*, vol. 89, pp 1441–1447 (1985).

Plueddemann, E.P., Summary of Excerpts from *Silane Coupling Agents*, Plenum Press, New York (1982).

Temofonte, T.A., et al., "Phthalocyanine semiconductor sensors for room–temperature ppb level detection of toxic gases," *Journal of Applied Physics*, vol. 65, No. 3, pp 1350–1355 (Feb. 1, 1989).

Wrighton, M.S., et al., "Preparation of Chemically Derivatized Platinum and Gold Electrode Surfaces. Synthesis, Characterization and Surface Attachment of Trichlorosilylferrocene, (1,1'–Ferrocenediyl)dichlorosilane, and 1,1'–Bis(triethoxysilyl)ferrocene," *Journal of the American Chemical Society*, vol. 100, No. 23, pp 7264–7271 (Nov. 8, 1978).

Wu, C.-G., et al., "Chemical Deposition of Ordered Conducting Polyaniline Film via Molecular Self–Assembly," *Chemistry of Materials*, vol. 9, No. 2, pp 399–402 (Feb. 1997).

Yamagishi, F.G., et al., "Conductive Polymer–based Sensors for Application in Nonpolar Media," *Polym. Mater. Sci. Eng.*, vol. 71, pp 656–657 (1994).

Yamagishi, F.G., et al., "Enhanced Stability, Reversibility and Sensitivity of Conductive Polymer–Based Volatile Organic Compound Sensors," *Electrochemical Society Proceedings*, vol. 97, No. 19, pp 103–108 (1997).

Yang, X.Q., et al., "Poly(heterocycle) Langmuir–Blodgett Films," *Langmuir*, vol. 5, pp 1288–1292 (1989).

Ma, Yi Long, et al., "Potentiometric selective determination of hydrogen sulfide by an electropolymerized membrane electrode based on binaphthyl–20–crown–6," *Analytica Chimica Acta*, vol. 289, pp. 21–26 (1994).

Cullen, D.C., R.S. Sethi, & C.R. Lowe, "Multi–analyte Miniature Conductance Biosensor," *Anal. Chim. Acta, 231*, 1990, 33–40.

Dave, B.C., et al., "Sol–Gel Encapsulation Methods for Biosensors," *Anal. Chem.*, 66, No. 22, 1994, 1120–1127.

Dong, S., Z. Sun., & Z. Lu, "A New Kind of Chemical Sensor Based on a Conducting Polymer Film," *J. Chem. Soc.*, Chem. Commun., 1988, 993–995.

Dong, S., Z. Sun., & Z. Lu, "Chloride Chemical Sensor Based on an Organic Conducting Polypyrrole Plymer," *Analyst, 113*, 1988, 1525–1528.

Foulds, N.C. & Lowe, C.R., "Enzyme Entrapment in Electrically Conducting Polymers," *J. Chem. Soc., Faraday Trans. 1, 82*, 1986, 1259–1264.

Gholamian, M., et al., "Oxidation of Formic Acid at Polyaniline–Coated and Modified–Polyaniline–Coated Electrodes," *Langmuir, 3*, 1987, 741–744.

Gorton, L., et al., "Amperometric Glucose Sensors Based on Immobilized Glucose–Oxidizing Enzymes and Chemically Modified Electrodes," *Anal. Chim. Acta, 249*, 1991, 43–54.

Guiseppi–Elie, A. & A.M. Wilson, "Microsensor Devices Formed From Transducer–Active Polymeric Thin Films," Proceedings 64th Colloid. and Surf Sci. Symp., Jun. 18–20, 1990, Leigh University, Lehigh, PA.

Hoa, D.T., et al., "Biosensor Based on Conducting Polymers," *Anal. Chem, 64*, 1992, 2645–2646.

Iwakura, C., Y. Kajiya, & H. Yoneyama, "Simultaneous Immobilization of Glucose Oxidase and a Mediator in Conducting Polymer Films," *J. Chem. Soc., 15*, Chem. Commun. 1988, 1019–1020.

Kajiya, Y., et al., "Glucose Sensitivity of Polypyrrole Films Containing Immobilized Glucose4 Oxidase and Hydroquinonesulfonate Ions," *Anal. Chem., 63*, 1991, 49–54.

Karagözler, A.E., et al., "Potentiometric Iodide Ion Sensor Based on a Conducting Poly(3–methylthiophene) Polymer Film Electrode," *Anal. Chim. Acta, 248*, 1991, 163–172.

Lu, Z., Z Sun, & S. Dong, "Study of $C10_4$–Selective Electrode Based on a Conducting Polymer Polypyrrole," *Electroanalysis* , 1, 1989, 271–277.

Lawrence, A.J. & G.R. Moores, "Conductimetry in Enzyme Studies," *Europ. J. Biochem., 24*, 1972, 538–546.

Malmros, M.K., J. Gulbinski, III, & W.B. Gibbs, Jr., "A Semiconductive Polymer Film Sensor for Glucose," *Biosensors, 3*, 1987/88, 71–87.

Matsue, T., et al., "Electron–transfer from NADH Dehydrogenase to Polypyrrole and Its Applicability to Electrochemical Ocidation of NADH," *J. Electroanal. Chem., 300*, Interfacial Electrochem., 1991, 111–117.

Matsue, T., et al., "An Enzyme Switch Sensitive to NADH," *J. Chem Soc.*, Chem. Commun. 1991, 1029–1031.

Nishizawa, M., T. Matsue, & I. Uchida, "Penicillin Sensor Based on a Microarray Electrode Coated with pH–Responsive Polypyrrole," *Anal. Chem., 64*, 1992, 2642–2644.

Sun, Z., & H. Tachikawa, "Enzyme–Based Bilayer Conducting Polymer Electrodes Consisting of Polymetallophthalocyanines and Polypyrrole–Glucose Oxidase Thin Films," *Anal. Chem., 64*, 1992, 1112–1117.

Umana, M. & J. Waller, "Protein–Modified Electrodes. The Glucose Oxidase/Polypyrrole System," *Anal. Chem., 58*, 1986, 2979–2983.

Wei, Y., et al., "Composites of Electronically Conductive Polyaniline With Polyacrylate–Silica Hybrid Sol–Gel Materials," *Chem. Mater., 7*, 1995, 969–974.

Yamagishi, F.G., et al., "Conductive Polymer–Based Transducers as Vapor–Phase Detectors," Proc. Of the SPE Annual Technical Conference and Exhibits, ANTEC 98, XLIV, 1998, 1335–1339.

* cited by examiner

SENSOR FOR CHEMICAL AND BIOLOGICAL MATERIALS

I. BACKGROUND OF THE INVENTION

1. Field of the Invention

This invention relates to the field of sensors for detecting biological agents such as toxins, viruses, spores, bacteria and other pathogens, and to detect chemical agents as well. More particularly, it pertains to the use of a morphological change in the material of the sensor when a target pathogen or vapor interacts with the sensor. The sensor is inexpensive, sensitive, selective, robust, and covertly deployable.

2. Description of the Related Art

The need for detection of chemical and/or biological agents in a variety of applications is acute. A number of methods have been developed which allow such detection. However, none of the methods described in prior art is quite acceptable, as discussed below.

The present invention, as subsequently discussed, applies the concept of using indicator molecules for such detection as these indicator molecules are first ensconced on electroconductive polymer carriers.

The concept of immobilizing indicator biomolecules onto conductive polymer substrates as well as the development of chemical and biological sensor devices that are based on electroconductive polymers in general is an area that has attracted considerable recent attention. See, for instance:

(1) A. Guiseppi-Elie, U.S. Pat. No. 5,766,934;
(2) M. Umana and J. Waller, Anal. Chem. 1986, 58, 2979–2983;
(3) N. C. Foulds and C. R. J. Lowe, Chem. Soc., Faraday Trans. 1 1986, 82, 1259–1264;
(4) C. Iwakura, Y. Kajiya and H. Yoneyama, J. Chem. Soc., Chem. Commun. 1988, 15, 1019;
(5) T. Matsue, et. al. J. Electroanal. Chem. Interfacial Electrochem. , 1991, 300, 111–117;
(6) M. Malmors, U.S. Pat. Nos. 4,334,880 and 4,444,892;
(7) M. K. Malmors, J. Gulbinski, III, and W. B. Gibbs, Jr. Biosensors, 1987/88, 3, 71.

However, all of these electroactive biosensors are designed to operate in aqueous environments, not in air. The present invention, as subsequently discussed, also allows for the detection of the chemical or/and biological agents in aqueous environments, but it has the further advantage of detecting these agents in gaseous environments, such as air, as well.

In general, these devices are formed from thin films of electroconductive polymer fabricated on a pattern of microsensor electrodes, which are, in turn, formed on an insulating substrate. Sensor devices that exploit the transducer-active responses of electroactive polymers may be conductometric, as discussed, for example, in:

(8) A. J. Lawrence and G. R. Moores, Europ. J. Biochem. 1972, 24, 538–546;
(9) D. C. Cullen, R. S. Sethi and C. R. Lowe, Anal. Chim. Acta 1990, 231, 33–40.

A number of ways to cause the transducer-active conductometric response has been described. The prior art teaches the use of the large change in electrical impedance for that purpose. See, for example:

(10) A. Guiseppi-Elie and A. M. Wilson, Proceedings 64th Colloid. and Surf Sci. Symp., Jun. 18–20, 1990, Leigh University, Lehigh, Pa.;
(11) T. Matsue, et. al., J. Chem. Soc., Chem. Commun. 1991, 1029–1031;
(12) M. Nishizawa, T. Matsue and I. Uchida, Anal. Chem. 1992, 64, 2642–2644;
(13) D. T. Hoa, et. al., Anal. Chem. 1992, 64, 2645–2646;
(14) Guiseppi-Elie, A. U.S. Pat. No. 5,312,762;

A conductometric response that accompanies oxidation and or reduction of the polymer, the amperometric response, has also been described. See, for example:

(15) L. Gorton, et. al., Anal. Chim. Acta 1991, 249, 43–54.

The use of redox mediation and/or electrocatalysis to cause the transducer-active conductometric response has been also described. See, for example:

(16) M. Gholamian, et. al., Langmuir, 1987, 3; 741;
(17) Y. Kajiya, et. al., Anal. Chem. 1991, 63, 49;
(18) Z. Sun and H. Tachikawa, Anal. Chem. 1992, 64, 1112–1117.

In particular, the potentiometric method, when the electrode potential change that accompanies changes in polymer redox composition is measured, was used. See, for example:

(19) S. Dong, Z. Sun, and Z. Lu, J. Chem. Soc., Chem. Commun. 1988, 993;
(20) S. Dong, Z. Sun , and Z. Lu, Analyst 1988, 113, 1525;
(21) Z. Lu, Z. Sun and S. Dong, Electroanalysis, 1989, 1, 271;
(22) A. E. Karagozler, et. al., Anal. Chim. Acta 1991, 248, 163–172;
(23) Y. L. Ma, et. al., Anal. Chim. Acta 1994 289 21–26.

As will be shown below, the detection of the chemical and/or biological agents in accordance with one aspect of the present invention measures transducer-active conductometric response as a result of a morphological change in a polymer film. None of the prior art mentioned above teaches or discloses the measurement of the response as a result of such change.

As subsequently discussed, another aspect of the present invention takes advantage of the encapsulation of indicator substances within sol-gel matrices. The encapsulation of indicator biomolecules within the pores of sol-gel matrices have been described and used for manufacturing of optical biosensors.

See, for example:

(24) Bakul C. Dave, et. al., Anal. Chem., 1994, 66, 1120A–1127A.

There are also several examples of conductive polymer composite films in sol-gel matrices. See,.for example:

(25) Y. Wei, et al., Chem. Mater., 1995, 7, 969.

Furthermore, conductive polymer based sensors have been developed for detecting volatile organic compounds in air, along with chemical weapon simulants. See, for example:

(26) F. G. Yamagishi, et al., Proc. of the SPE Annual-Technical Conference and Exhibits, ANTEC 98, XLIV, 1335 (1998).

Other sensor technologies include surface acoustic wave devices (which require complex frequency counting electronics), mass spectroscopy, infrared spectroscopy, and gas chromatography, or some combination or combinations of these methods. These techniques are currently being developed but are primarily directed toward laboratory analysis rather than field application. All of the existing methods of analysis and detection of biological pathogens and chemical agents have serious disadvantages of having large size, long analysis times, complicated electronics support, lack of specificity and high cost.

In view of the foregoing, there is a need for a simple, inexpensive and accurate sensor for detection of biological pathogens and chemical agents. A sensor is needed which is also low power, compact, rugged, highly selective, and adaptable to field application for detection of vapor phase pathogens in real time without the need for involving "wet" chemistry. There is no known prior art which teaches a sensor satisfying all these requirements.

The present invention provides such a sensor by combining conductive polymer transducers and encapsulated sol-gel techniques. The combination of these approaches is not found in any other sensor device for the detection of biological or chemical materials.

II. SUMMARY OF THE INVENTION

The present invention provides a sensor that can detect biological pathogens and chemical agents with unsurpassed sensitivities in the sub-part-per-million range, and possibly into the sub-part-per-billion regimes with good selectivity (low false alarm rate) in the vapor state in real time.

The sensor of the present invention avoids the problems with selectivity and has further advantages by operating passively in an ambient atmosphere without the need for concentrators to detect pathogens in air. Furthermore, the sensor of this invention can be equipped with communication capability so that a multitude of sensors could be deployed and their position and response to the environment, as communicated to a central control site, would provide a mapping of any potential hazard.

In accordance with one aspect of this invention, the sensor comprises a dielectric substrate, on which metal interdigitated (comb-like) electrodes are deposited. The substrate having such electrodes is then further coated with a thin film derived from the coupling of a conductive polymer and a sol-gel-derived material. The conductive polymer acts as the tranducer and the sol-gel material encapsulates, or is attached to, an indicator biomolecule (e.g., enzyme, antibody, antigen, etc.) specific to interacting with the target pathogen.

The conductive polymer comprises linear, highly conjugated polymers, which have an ability to conduct electricity by generating (by being oxidized or reduced) unpaired electrons traveling along the n-electron cloud of such a highly conjugated system. The conductivity is anisotropic in nature and is greatest in the direction along the chain, although there is some cross-talk between the adjacent polymeric chains, especially in macroscopic cases.

When the conductive polymer is prepared as a thin film, the direction of its polymeric chains is random, thus making an overall morphology of such thin polymeric films essentially amorphous.

The interaction-of the indicator biomolecule and the pathogen causes a morphological alteration in the material of the sensor because of a redistribution of the chains, with respect to each other, even on a microscopic scale, resulting in changes in distances between the chains and in the degree of cross-talk. Any influence causing a morphological change in the conductive polymer leads to a modulation of the conductivity of such a polymer. This modulation is detected by applying a voltage and registering the change in current.

The interaction of the indicator of chemical substances and the chemical substance may likewise cause a morphological alteration in the conductive polymer material of the sensor. Thus, chemical substances having toxic or pathogenic effects to certain biological moieties can be detected through this technique of the morphological alteration followed by the registering the conductivity modulation. For instance, some organophosphorus molecules (i.e., fungicides, insecticides, nerve-paralytical gases) selectively interact with acetylcholineesterase so that the latter can be immobilized and used as an indicator molecule for these organophosphorus compounds. Other indicator molecules can detect, in the same fashion, mixtures of even relatively inert aromatic hydrocarbons, such as benzene, toluene, ethylbenzene, and xylene.

III. BRIEF DESCRIPTION OF THE DRAWINGS

The features and advantages of the present invention will become better understood with regard to the following description, appended claims, and accompanying drawings where FIG. 1 is an elevation view schematic diagram showing the architecture of the sensor.

Figure 2A:
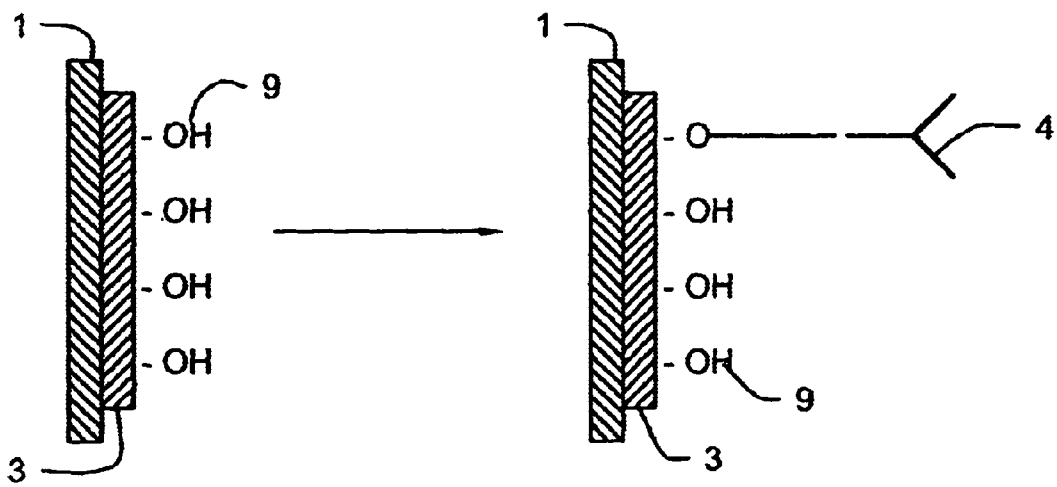
Figure 2B:
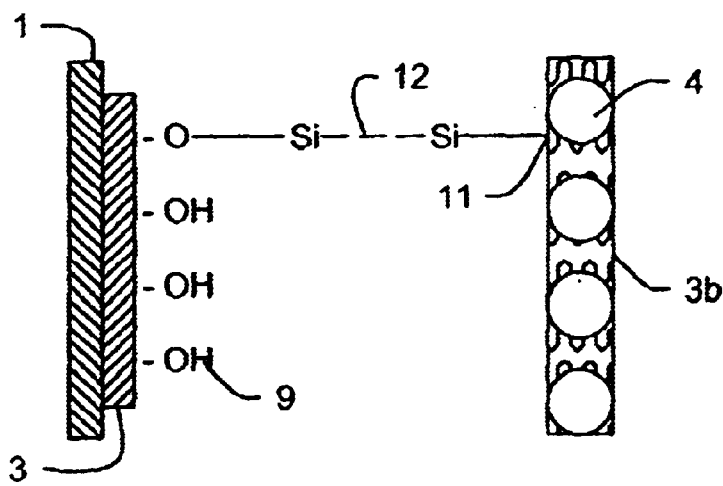

FIGS. 2(a) and 2(b) are schematic diagrams showing the tethering of a sol-gel containing encapsulated indicator biomolecules to a hybrid material or a sol-gel matrix.

TABLE A is a list of abbreviations used to describe chemical materials used in this invention.

TABLE 1 demonstrates a summary of the materials used to prepare the sensor of this invention and some of their adhesive and conductive properties.

TABLE 2 summarizes properties of some conductive polymer sol-gels used in this invention.

TABLE 3 demonstrates response factors for some sol-gel sensors where the enzyme glucose oxidase is used as the bioindicator molecule.

IV. DETAIL DESCRIPTION OF THE INVENTION

The sensor which is the subject matter of the present invention preferably comprises a conductive polymer transducer and indicator biomolecules encapsulated in a sol-gel-derived material.

1. The Sensor in General

Figure 1:
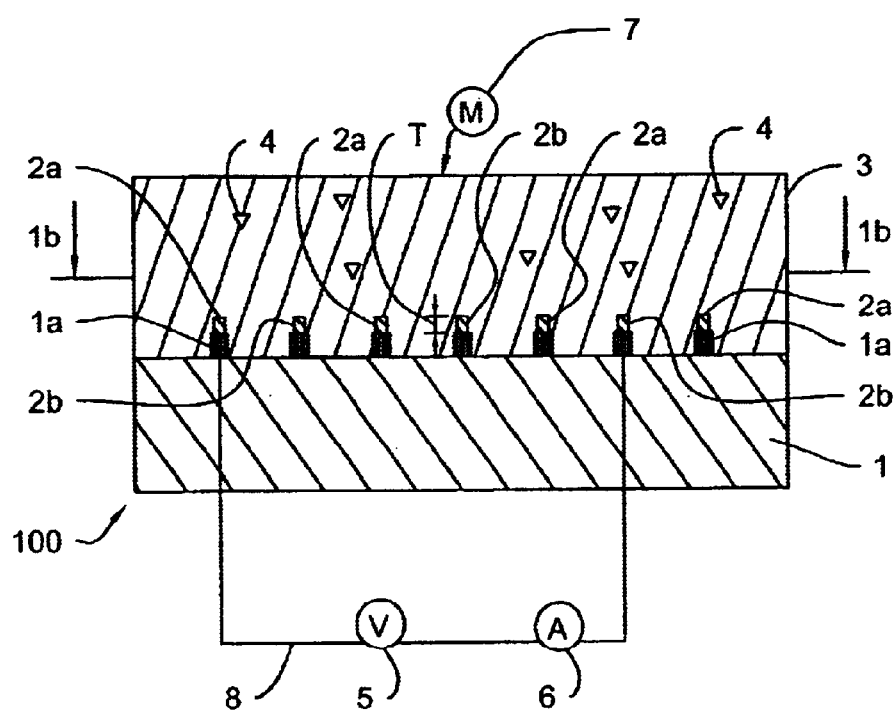
FIG. 1(a) is a schematic diagram showing the location of the electrodes of the sensor.
FIG. 1(b) is a schematic diagram showing a plan view of the electrodes when viewed along the 1b—1b line of FIG. 1
Figure 1A:
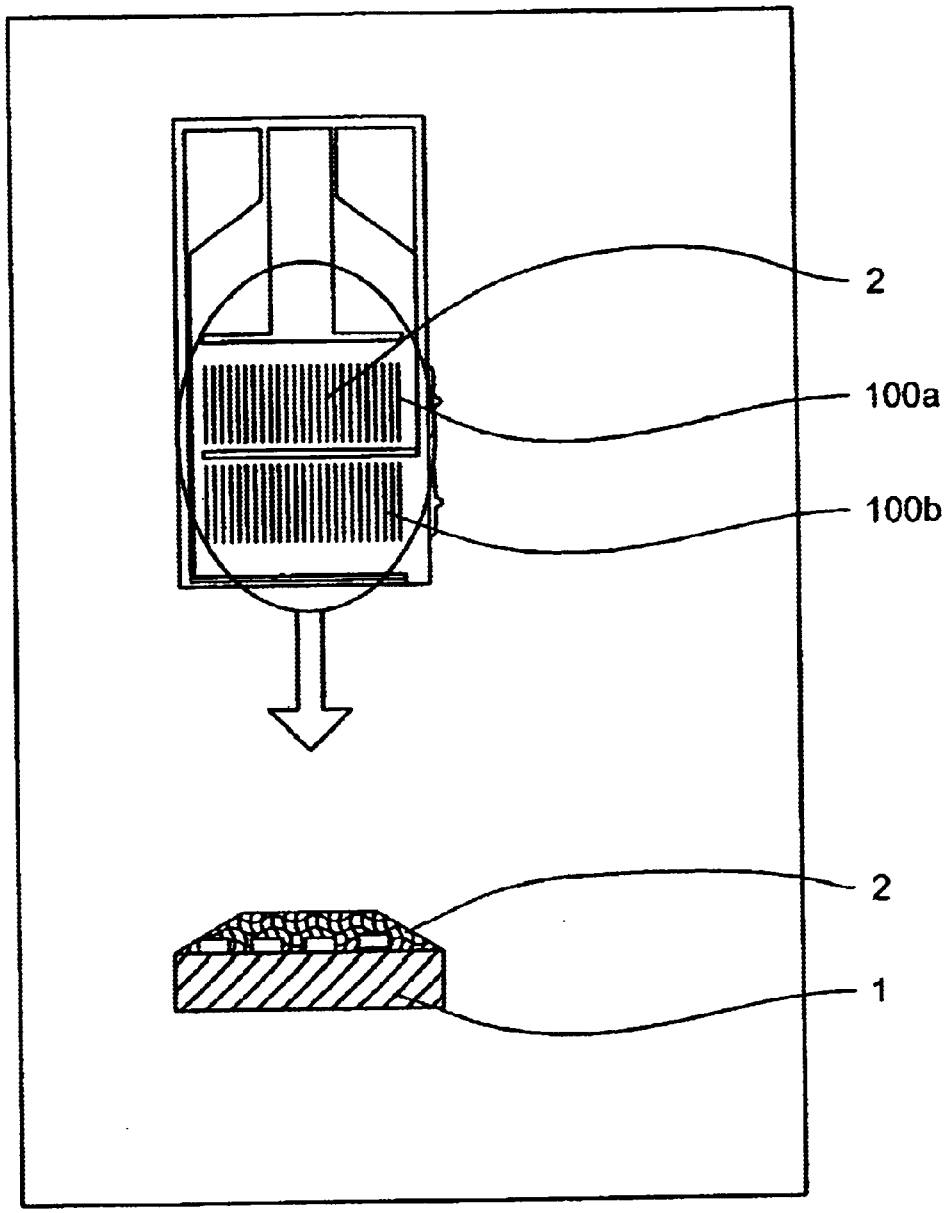

FIG. 1 shows schematically the structure of an embodiment of the sensor 100. Generally, one sensor element is present on a dielectric, substrate 1, but more than one sensor can be present in a particular assembly. For example, FIG. 1(a) shows a dielectric substrate 1, which can be commercially available (for instance, ABTECH Scientific) and which contains two sensor elements 100a and 100b combined in one assembly to be subsequently discussed. Such two sensor element assembly was used for tests discussed. hereinafter.

Two identical sensor elements can be provided in one assembly or two separate sensor elements can be utilized. In such case one would preferably be used for measurements while the other sensor will preferably act as a reference. A sensor element containing only one sensor, and, therefore, only one set of subsequently discussed interdigitated electrodes is completely acceptable and adequate in some embodiments. Those skilled in the art will determine the number of sensors used in the assembly, which number will be suitable for a particular use.

Figure 1B:
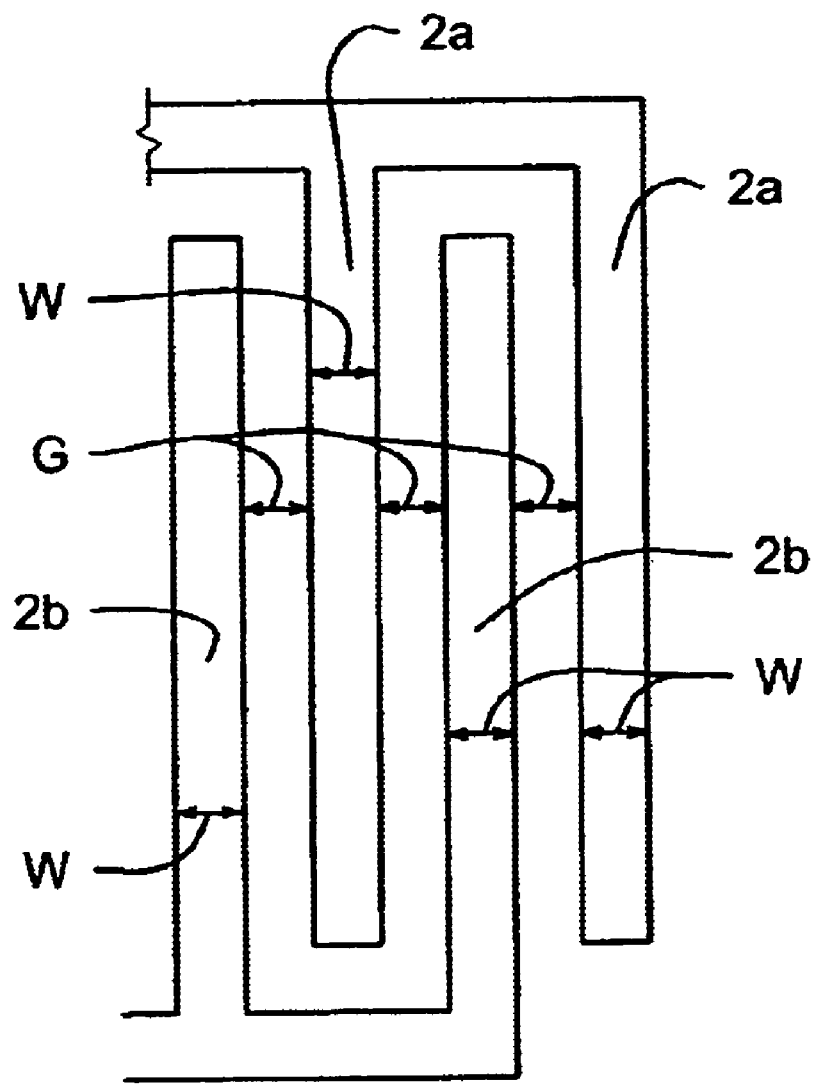

Metal interdigitated electrodes 2 are deposited on a dielectric substrate 1. A material of which dielectric substrate 1 is made comprises any dielectric material, such as glass, ceramic, or plastic, each of these dielectric materials being, generally speaking, equally, preferable. The choice of a particular substrate will be made by those skilled in the art according to the needs of a particular application. The thickness of the dielectric substrate 1 ranges from preferably about 5 micrometers (in case a plastic used as the dielectric substrate 1) to preferably about 2 millimeters (in case of a glass or ceramic dielectric substrate 1). Interdigitated electrodes 2, comprising digits 2a and 2b, are made of any material conducting electricity, but preferably are made of gold, due to gold's good conductivity and general inert nature. Modulation of the conductivity, upon which detection of biological and/or chemical materials depends, is accomplished by a modification of the morphology of the material in the gaps G between the digits 2a and 2b (see FIG. 1(b)). If the size of the gaps G is too large, then it becomes difficult to prepare films that uniformly fill this gap through the complete dimension of the electrode set. If the thickness of the digits 2a and 2b is low, less conductive material is necessary to fill the gaps, but that results in a reduced absolute electrical signal. The electrode configuration shown in FIGS. 1(a) and 1(b), and described below, is adequate in order to be able to both prepare the films uniformly by filling the gaps and to obtain a sufficiently strong electrical signal.

The shape of the electrodes 2 is preferably rectangular in cross section. As mentioned above, each electrode 2 comprises a plurality of digits 2a and 2b, the digits interleaving as shown on FIG. 1(b). The width W of each gold digit 2a and 2b is within a range of between about 5 micrometers and about 25 micrometers, preferably about 15 micrometers. The gaps G between the digits 2a and 2b are within a range of between about 5 micrometers and about 25 micrometers, preferably about 15 micrometers. The thickness T of each digit 2a and 2b is within a range of about 1 micrometers to about 4 micrometers, as shown on FIG. 1. About 50 line pairs of digits 2a and 2b are preferably used, but the number of such line pairs can vary with the application and the dimensions of the sensor element required for a particular application.

The electrode pattern described above and shown in FIGS. 1(a) and 1(b) is made by standard semiconductor processing known to those skilled in the art. For example, a clean glass substrate 1 is coated with a thin layer of titanium or titanium/tungsten alloy 1a, preferably by sputtering. This layer 1a, the thickness of which is preferably about 100 Angstroms, acts as an adhesion layer for the gold electrode. The next step is deposition of a layer of gold having a thickness within a range of between about 1 micrometer and about 4 micrometers, either by sputtering or evaporation. A photoresist (not shown) is applied to the bilayer thus formed, which photoresist is patterned to the desired electrode configuration using a lithographic mask (not shown). Once the pattern is formed by the photoresist, the gold is removed from the substrate by etching away the gold and layer 1a, preferably by sputter etching, after which the resist is removed leaving the complete set of highly adhering interdigitated electrodes 2 disposed on the remainder of the thin layer of titanium or titanium/tungsten alloy 1a.

The electrodes 2 are coated with a thin composite film 3 comprising a conductive polymer component and a sol-gel-derived material component. The thickness of composite film 3 is within a range of between about 0.5 micrometers and about 20 micrometers, preferably within a range of between about 3 micrometers and about 7 micrometers.

Examples illustrating the preparation the composite film are discussed below.

The sol-gel material has many distinct advantages. Indicator molecules can be readily encapsulated within the cavities of a sol-gel matrix by relatively simple methods. Bioindicator molecules such as enzymes, antibodies, antigens, or DNA can be encapsulated. Since these molecules can be chosen for their interaction or reaction with only their conjugate, specificity is rendered to the sensor even in the presence of other possibly interfering pollutants or pathogens.

For those bioindicator molecules which have an intrinsic steric conformation (i.e., coiled structure) that determines their biological activity, their stability can become compromised with increasing temperature resulting in a modification of their conformation (i.e., uncoiling or denaturation) and therefore a loss in activity. Encapsulation of these indicator molecules in a sol-gel matrix, however, precludes this process since the molecules are confined within the cell of the sol-gel making it more difficult to denature. This results in enhanced thermal stability. Further, these molecules require an aqueous environment for their viability. During the encapsulation process, water is also captured with the indicator molecule which then also enhances the stability of the indicator molecules. The resulting sol-gel film, however, is dry to the touch. Thus, an external supply of aqueous medium is not required to retain the viability of the indicator molecule which greatly reduces the complexity of the resulting sensor element.

Very close contact between the conductive polymer component and the sol-gel derived material component is very desirable and is achieved by bringing these two components into such close contact through covalent bonding, or through dispersing of the conductive polymer within the polymer matrix formed by the sol-gel derived material component. Using a single thin composite film 3 where the conductive polymer component and the sol-gel derived material component are in such close contact is preferred. Alternatively, it is also possible to use a composite film 3 where the conductive polymer component and the sol-gel derived material component form two distinct and separate films, and these films are in very close contact which is a cohesion-type contact.

Two methods of preparation of the sol-gel derived component of the conductive polymer-sol-gel composite film 3 are discussed below.

According to a first method, hybrid sol-gel materials are prepared, that is, those materials that contain an inorganic sol-gel matrix attached to an organic polymeric chain. They are prepared by the polymerization of a monomer which contains inorganic moieties capable of forming a sol-gel. An example of such hybrid sol-gel material is a copolymer of 3(trimethoxysilyl)propylmethacrylate (MSMA) and methylmethacrylate (MMA) and this copolymer is synthesized by radical copolymerization of the two monomers in the presence of benzoyl peroxide as a catalyst.

This copolymerization is conducted according to a known procedure and is shown schematically as follows:

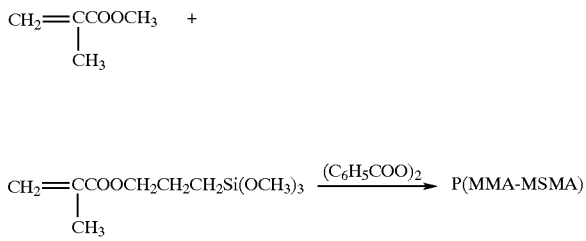

The pendant siloxyl groups are then converted into a sol-gel leading to a hybrid material. A more detailed description of the preparation of the composite conductive polymer-sol-gel material is discussed below.

The sol-gel matrix composed of only silicon and oxygen atoms can also be used successfully in this invention. Thus, starting materials that do not contain a polymeric backbone (as those used to prepare hybrid sol-gels) such as, but not limited to, tetramethoxysiloxane, methyltrimethoxysilane, n,p-styrylethyltrimethoxysiloxane, and glycidoxypropyltri-methoxysiloxane can also be used and can be chosen by the particular sensor application requirements.

The conductive polymer component of the composite film 3 comprises polyaniline, polythiophene, or polypyrrole and their derivatives. The selected conductive polymer is soluble so that it will phase-separate properly in the forming sol-gel. Also, it is desirable that the conductive polymer, in some cases, be soluble in water to keep the bioindicator molecules viable. Many bioindicator molecules are not stable in organic solvents. Usually, large surfactant-type molecules (usually containing sulfonate groups) result in enhanced solubility of conductive polymers in organic solvents. In some cases, using polymeric surfactants (e.g., polystyrenesulfonate) and incorporating sulfonate groups into the conductive polymer backbone can result in water solubility. Particular examples of some conductive polymers are subsequently discussed.

According to another method of obtaining a composite film 3 is to bring P(MMA-MSMA) (prior to gelation) into contact with a conductive polymer, e.g.,polyaniline campho-sulfonic acid, the conductivity of which is retained following formation of the sol-gel according to the following procedure.

Polyaniline camphosulfonate is ground to form a powder, with particles having a size of about 10 micrometers, followed by dissolving the powder in an appropriate aromatic solvent, preferably, meta-cresol. The resulting solution of polyaniline camphosulfonate is then mixed with P(MMA-MSMA) described above to form a final conductive hybrid material following the evaporation of the solvent and gelation. Particular examples of some conductive hybrid materials obtained by this method are subsequently discussed.

The polyaniline-based conductive polymer forms an interpenetrating type of three-dimensional network throughout the hybrid material. Thus, the conductive polymer is intimately intertwined throughout the sol-gel matrix and is capable of detecting any changes to the structure of the sol-gel.

An indicator biomolecule 4 is encapsulated ir the sol-gel-derived material and thus in composite material 3. Such encapsulation of the indicator biomolecule 4 takes place during the formation of the hybrid material described above and is achieved by introducing the appropriate substance (e.g., enzyme, antibody, DNA, etc.) prior to the gelation step. An example of a particular biomolecule used in the preferred embodiment of this invention, glucose combined with an enzyme glucose oxidase, is discussed susequently.

If a particular indicator biomolecule 4 is not compatible with an essentially non-aqueous solvent (like meta-cresol), which solvent is preferably used to dissolve the conductive polymer, then conductive polymers that are soluble in less corrosive solvents are used, for instance, polyaniline-dodecylbenzenesulfonic acid complex, or polyaniline co-doped with dodecylbenzenesulfonic and hydrochloric acids. Water soluble adducts of polyaniline can be also used. In such application, less corrosive non-aqueous solvents or water are used in preparation of the hybrid material.

Thus, a single composite, or polymer blend, film 3 containing a conductive polymer transducer and an indicator biomolecule 4 encapsulated within a sol-gel matrix is obtained. The most efficient transduction occurs when the encapsulated bioindicator molecule 4 is in close proximity to the conductive polymer. If the subsequently discussed tethering approach is implemented, there is increased distance between the encapsulated bioindicator molecule 4 and the conductive polymer. The transduction will still occur, but it is possible that the sensitivity might be compromised, and the method might be less efficient than predicted. In such case of lesser than predicted efficiency, an alternative embodiment-of encapsulation of the indicator biomolecule 4 can be used. According to such alternative method of encapsulation, the indicator biomolecule 4 is encapsulated "externally," in a stand-alone sol-gel matrix 3b, which then is tethered to the composite film 3, as shown on FIG. 2(b). This tethering is achieved through residual hydroxyl groups that are present on both composite film 3 (indicated as numeral 9) and on encapsulating sol-gel matrices 3b (indicated as numeral 11). A commercially available disilyl crosslinking coupling agent available from Aldrich Chemical Co., Petrarch Systems, Inc., Huls America, or Union Carbide Chemicals is used for this purpose.

As shown on FIG. 2(a), the tether 10 would connect the surface of conductive polymer to the indicator biomolecule 4 allowing a conductivity change when the latter interacts with a pathogen.

An additional embodiment is shown on FIG. 2(b) and demonstrates that the external sol-gel 3b, through its surface hydroxyl groups 11, can be incorporated into the forming gel of the P(MMA-MSMA) pendant alkoxysilyl groups during its gelation through the formation of a silicon-silicon bridge 12.

The sensor 100, as shown on FIG. 1, is equipped with a source of voltage 5 and an ammeter 6. When a chemical or biological molecule of the agent to be detected 7 approaches the sensor 100, it interacts with indicator biomolecule 4 causing morphological changes in the thin composite film 3. These changes in turn change the conductivity of the conductive polymer. As a result, the electrical current in circuit 8 changes which change is registered by the ammeter 6.

The sensor elements 100a and 100b are monitored by applying a voltage and reading out the change in current. The voltage can be applied by a nominal power supply (e.g., external or designed into circuitry, or a battery). Both alternating and direct current sources are acceptable. Similarly, the output current can be monitored by an external ammeter or one designed into circuitry. Electronic designs in which the power supply and ammeter are integrated into circuitry is preferred.

If the applied voltage is too low, the resulting output current is too low (resulting in increased electrical noise); and if the applied voltage is too high, the possibility of electrochemical degradation of the conductive polymer increases. The amount of voltage used is within a range of between about 5 millivolts and about 300 millivolts, preferably, between about 10 millivolts and about 50 millivolts. The sensitivity of the measurement of the current is within ±2 nanoAmperes for a sensor with the size of about 1 centimeter by 1.5 centimeter.

2. Preferred Embodiments of the Sensor.

Preferred embodiments of the present invention are described below.

Glucose oxidase (GOD) was used as the indicator biomolecule 4. In this system, only glucose is oxidized in the presence of GOD to produce gluconic acid and hydrogen peroxide. In all examples that follow, glucose was used as the analyte or the agent to be detected 7. As a result of this reaction of oxidation, morphological changes occur producing a desired modulation of the conductivity of the conductive polymer.

The list of abbreviations used in the following discussion is presented in Table A.

A. Conductive Polymer Sol-Gels (C-gels).

Sol-gel matrix, composite films 3 containing only conductive polymer (so-called C-gels) were prepared, and it was determined that composite films 3 displayed good conductivity and adhesion and could be later co-encapsulated with the bioindicator material 4 as described below. A summary of some of the materials prepared and an assessment of their adhesive and conductive characteristics is presented in Table 1.

The conductive polymer and siloxane were mixed in a small vial followed by sonication for 3 to 5 minutes before allowing the mixture to cure. Sol-gel formation was accomplished by either casting the resulting solution into an open evaporating dish, or casting 50 to 100 microliters of the solution onto a glass slide, or casting 5 microliters onto a glass slide cover or onto interdigitated electrodes 2. Samples were allowed to cure by standing exposed for at least 1 to 5 days, under ambient conditions in a laboratory fume hood. Conductivity measurements were then made on the cover slide samples using the van der Pauw method and adhesion was assessed by visual inspection of the glass slide samples after curing. Adhesion was considered acceptable if there was no cracking or peeling of the film after curing, and there was no peeling upon their exposure to liquid water.

Samples used as C-gels in the formulation discussed below were first scraped from the evaporating dish or glass slide after curing, thoroughly dried at 50° C. for 16 to 72 hours and then finely ground. Properties of some C-gels are demonstrated in Table 2.

B. Co-Encapsulated Conductive Polymer and Enzyme.

Co-encapsulation of the conductive polymer and bioindicator material 4 was accomplished using one of three basic approaches. Under every approach used, a single thin composite film 3 was formed where the conductive polymer component (from C-gel) and the sol-gel derived material component (from E-gel) are bonded in silicon matrix through covalent bonding.

Under the first approach (Method 1), both the conductive polymer and enzyme were first formed as separate sol-gels (designated C-gel and E-gel, respectively). These two gels were then co-encapsulated in a second gel matrix forming a so-called secondary (2°) gel. Alternatively, the conductive polymer was encapsulated directly with the E-gel, but since enzymes typically require buffered conditions to prevent denaturation, such an approach is suitable only with water soluble or dispersible conductive polymers with moderate pH. Another more general approach avoids the requirement that the conductive polymer be soluble in the sol mixture used to make the 2° gel, which allows the use of a larger number of conductive polymers. This involves first encapsulating both the conductive polymer and the enzyme separately, which minimized deactivation of the enzyme by the protection provided by the silica matrix of the E-gel.

Conductive polymers with excess counterions are toxic to the enzymes. Similarly, C-gels prepared from these materials proved toxic to the encapsulated enzyme. However, such C-gels may be extracted to remove excess acid, which increased the pH to an acceptable level. For GOD, a pH range of 4 to 7 is considered suitable for maintaining its viability. Therefore, in a modification to this first approach, C-gels were extracted with water to provide a suitably acid-free material for co-encapsulation with E-gel either with or without the use of buffer.

Example 1. Preparation According to Method 1.

E-gel containing about $9.1 \times 10^{-4}\%$ of GOD, and C-gel containing between about 2.5% and about 50% by weight of conductive polymer were incorporated into another sol-gel composed of a 2:1 or a 1:1 molar mixture of TMOS and either SETMOS or GPTMS. This stock solution (a secondary siloxane) was then mixed with water and hydrochloric acid according to the following ratio:

| | |
|---|---|
| Stock solution (TMOS/SETMOS or TMOS/GPTMS) | 0.100 mol |
| $H_2O$ | 0.190 mol |
| HCl | 0.009 mol |

The stock solution so treated is then used to form a 2° gel, encapsulating C- and E-gels according to the following ratio:

| | |
|---|---|
| Treated stock solution | 100 mg |
| C-gel | 650 mg |
| E-gel | 20 mg |

Alternatively, the method described in Example 1, can be used with a buffer solution to enhance the viability of the immobilized enzyme. The pH 6 buffer solution is first added to the treated stock solution in the ratio of 0.55 milliliters of the buffer solution per 0.45 milliliters of the treated stock solution, and then the buffered stock solution is used to form a buffered 2° gel, encapsulating C- and E-gels according to the following ratio:

| | |
|---|---|
| Buffered treated stock solution | 200 mg |
| C-gel | 650 mg |
| E-gel | 20 mg |

Example 2. Preparation According to Method 2.

The second approach (Method 2) is similar to Method 1 except that the conductive polymer is not used as a C-gel, but instead is incorporated directly into the secondary gel. Activity testing on gel materials prepared using this second approach indicated that the pH of the gelation process is important not only for gel formation, but also for enzyme stability. Conductive polymers such as polyaniline with dodecylbenzene sulfonic acid counterion (Pani-DBSA) and a polythiophene derivative with polystyrene sulfonic acid counterion (PEDOT-PSSA) require excess counterion to provide solutions of the conductive polymers suitable for preparing a C-gel. However, this excess acid material proved to be toxic to the enzyme during the preparation of the 2° gel, resulting in a significant reduction in the activity of sensors prepared from these materials. Preliminary sensor response test results with transducers so prepared demonstrated responses to glucose that were apparently attenuated by the extent to which the enzyme had been deactivated due to this problem (see below). This problem was resolved by using conductive polymers with no extractable counterion and by performing the co-encapsulation of conductive polymer and E-gel in a buffered sol.

A C-gel is formed and simultaneously incorporates a previously formed E-gel during the process. Both gels are prepared in the same way as described in Example 1, above, and the same stock solution is also used. A conductive polymer is buffered with a buffer solution described in Example 1, above. A 2° gel is then formed encapsulating E-gels according to the following ratio:

| | |
|---|---|
| Treated stock solution | 100 mg |
| Conductive polymer | 100 mg |
| E-gel | 50 mg |

Alternatively, the method described in Example 2, can be also used with a buffer solution. Conductive polymer is first dissolved as a 2% solution in a pH 6 buffer and then mixed with the treated stock solution of secondary siloxane and E-gel as follows:

| | |
|---|---|
| Treated stock solution | 500 mg |
| Conductive polymer (buffered) | 500 mg |
| E-gel | 50 mg |

The approach of Method 2 allowed better dispersing and mixing of conductive polymer and enzyme in the sol-gel network than that of Method 1.

Example 3. Preparation According to Method 3.

Under the third approach (Method 3), the conductive polymer was encapsulated directly with the enzyme in a so-called primary gel. This approach is preferred in that the most intimate mixture of conductive polymer and enzyme will result, but is limited in scope in that only water-soluble (i.e., buffer soluble) conductive polymers are suitable. Method 3 afforded the most intimate mixing of a conductive polymer and enzyme to form a buffered primary gel, containing GOD.

A conductive polymer, in a form of a 1% to 10% aqueous solution was added to the sol, which had been previously buffered, as described in Example 2, above. An enzyme (GOD) stock solution of about 1.46 mg/ml in a pH 6 buffer was then added as follows:

| | |
|---|---|
| Treated stock solution | 0.45 ml |
| Conductive polymer | 13.00 mg |
| pH 6 buffer | 0.55 ml |
| GOD stock solution | 1.00 ml |

For each approach, a standardized method for preparation of the various gels was developed. Gel formulations were mixed and cast onto glass slides or interdigitated electrodes 2 using the procedures similar to those described for the preparation of C-gels above. These procedures resulted in active gels in many cases and provided good adhesion and conductivity characteristics for use in subsequent sensor response tests.

A summary of the formulation methods as well as conductivity, adhesion, and activity characteristics are presented in Table 1.

C. Evaluation of Transducer Response

Sensor transducers comprising sol-gel encapsulated GOD composited with conductive polymers were prepared and tested for glucose response. The results of the tests are summarized in Table 3.

These sensors were prepared in accordance with Method 2 described in Example 2, and contained about $3.4 \times 10^{-5}\%$ of glucose oxidase and about 3.64% of siloxane, with between about 1% and about 1.3% conductive polymer. Sample transducers were prepared by casting about 5 microliters of this mixture onto gold interdigitated electrodes 2 and the resulting gel was then cured for between 1 to 3 days before testing against glucose in aqueous solution.

The glucose response characteristics of these transducer materials were determined in experiments in which sensors were immersed in 60 ml of a pH 7 buffer and allowed to equilibrate to a steady-state baseline. Measured amounts of glucose (as a 10% solution), or hydrogen peroxide (as a 30% solution) were added with stirring and the change in conductivity of the transducer was recorded. Addition of 60 milligrams of glucose provided a glucose exposure (increase) of 1 part per thousand (ppt), while addition of 10 microliters of $H_2O_2$ resulted in an increase of 50 parts per million.

Having described the present invention in connection with several embodiments thereof, modification will now suggest itself to those skilled in the art. As such, the invention is not to be limited to the described embodiments except as required by the appended claims.

TABLE A

| | Abbreviations |
|---|---|
| PEDOT-PSS | Poly(ethylenedioxythiophene) polystyrene sulfonate |
| PAS | Poly(anilinesulfonic acid) |
| Pani-DBSA | Polyaniline dodecylbenzene sulfonate |
| Pani-CSA | Polyaniline camphor sulfonate |
| Pani-FA | Polyaniline formate |
| Pani-dNNSA | Polyaniline dinonylnapthyl sulfonate |
| P(MMA-MSMA) | Poly[methylmethacrylate-co-3-(trimethoxysilyl)propyl methacrylate] |
| TMOS | Tetramethoxysiloxane |
| MTMOS | Methyltrimethoxysilane |
| SETMOS | n, p-styrylethyltrimethoxysiloxane |
| GPTMS | glycidoxypropyltrimethoxysiloxane |

TABLE 1

Development Matrix for Sensor Transducer Formulation

| | Encapsulation Approach | | | | | | | | |
|---|---|---|---|---|---|---|---|---|---|
| | 2° Gel w/ E-Gel (Methods 1 & 2) | | | Buffered 2° Gel w/ (E-Gel) | | | Buffered 1° Gel w/ GOD (Method 3) | | |
| Conductive Polymer as | Ac[1] | C[2] | Ad[3] | Ac | C | Ad | Ac | C | Ad |
| Conductive Polymer Gel (C-Gel)[4] | | | | | | | | | |
| PAS | | | | | | | | | |
| w/ TMOS/MTMOS (1:40)[5] | ++ | ND | D | | | | | | |
| w/ TMOS/MTMOS (1:10)[5] | + | ND | D | | | | | | |
| w/ TMOS/MTMOS (1:1) | + | 1 | A | | | | | | |
| Pani-CSA | | | | | | | | | |
| w/ P(MMA-MSMA) (1:1) | + | ND | A | | | | | | |
| w/ P(MMA-MSMA) (4:1) | | | | | | | | | |
| Pani-DBSA/1DBSA (washed) | | | | | | | | | |
| w/ TMOS (1:1) | − | ND | ND | | | | | | |
| w/ TMOS (1:33) | + | ND | ND | | | | | | |
| PEDOT-PSSA (washed) | | | | | | | | | |
| w/ TMOS (1:0.38) | | | | | | | | | |
| w/ TMOS (1:38.5) | | | | | | | | | |
| Pani-dNNSA (washed) | | | | | | | | | |
| w/ TMOS (1:40) | | | | | | | | | |
| Pani-FA (washed) | | | | | | | | | |
| w/ TMOS (1:40) | | | | | | | | | |
| Conductive Polymer Solution[6] | | | | | | | | | |
| PEDOT-PSSA | | | | | | | | | |
| (1:4)[5] | + | 8 | C | | | | | | |
| PAS | | | | | | | | | |
| (1:10)[8] | + | ND | D | | | | | | |
| (1:1) | | | | + | 8[7] | A | | | |
| (1:10) | | | | ++ | 1 | A | ND | 5 | B |
| Pani-dNNSA (1:40) | | | | | | | | | |

[1]Activity (Ac): ++, +, − (highly active, slightly active, or inactive as determined by color test)
[2]Conductivity (C): 1–10 (low to high relative rating for cured transducer in lab air)
[3]Adhesion (Ad): A–D (good to bad relative rating for cured slide immersed for 30 min. in pH 6 buffer).
[4]Weight ratio given for conductive polymer to siloxane in C-gel.
[5]Used TMOS blended with DMS/EO (1:1 weight ratio) as the 2° siloxane.
[6]Weight ratio given for conductive polymer to total 2° siloxane.
[7]Polymer leached out during immersion in buffer resulting in conductivity decrease to '3' rating.
[8]Used TMOS blended with MTMOS (1:1 weight ratio) as the 2° siloxane.

TABLE 2

Properties of Some Conductive Polymer Sol-Gels (C-Gels)

| | Weight Ratio of Conductive Polymer-to-Siloxane | | | | | Rating of Property | |
|---|---|---|---|---|---|---|---|
| Conductive Polymer | TMOS + MTMOS (1:1) | TEOS + H2O + DBSA (4:1:2) | TMOS + p DMS/EO (1:1) | TMOS + GPTMS (1:1) | P(MMA-MSMA) (4:1) | Adhesion | Conductivity, S/cm |
| Poly(ethylenedioxythiophene) polystyrene sulfonate (PEDOT-PSS)[1] | 1:38.5 | | | | | Hard, badly cracked, not adhered | ND |
| | | | 1:2.6 | | | Crack-free, uniform, well adhered (slightly tacky) | |
| Poly(anilinesulfonic acid) (PAS)[2] | 1:40 | | | | | Hard, badly cracked, not adhered | ND |
| Poly(anilinesulfonic acid) (PAS)[2] | 1:10 | | | | | Hard, badly cracked, not adhered | ND |
| Poly(anilinesulfonic acid) (PAS)[2] | | | | 1:10 | | Crack-free, uniform, well adhered (slightly tacky) | ND |
| Polyaniline dodecylbenzene sulfonate (Pani-DBSA)[3] | 1:3 | | | | | Hard, badly cracked, not adhered | ND |

TABLE 2-continued

Properties of Some Conductive Polymer Sol-Gels (C-Gels)

| Conductive Polymer | Weight Ratio of Conductive Polymer-to-Siloxane | | | | | Rating of Property | |
| --- | --- | --- | --- | --- | --- | --- | --- |
| | TMOS + MTMOS (1:1) | TEOS + H2O + DBSA (4:1:2) | TMOS + p DMS/EO (1:1) | TMOS + GPTMS (1:1) | P(MMA-MSMA) (4:1) | Adhesion | Conductivity, S/cm |
| Polyaniline dodecylbenzene sulfonate (Pani-DBSA)[3] | 1:1 | | | | | Tactile, badly cracked, poor adhesion | ND |
| Polyaniline dodecylbenzene sulfonate (Pani-DBSA)[3] | | 1:2 | | | | Tactile, badly cracked, poor adhesion | ND |
| Polyaniline dodecylbenzene sulfonate (Pani-DBSA)[3] | | | 1:1 | | | Some cracking, tactile, good adhesion | |
| Polyaniline dodecylbenzene sulfonate (Pani-DBSA)[3] | | | | 1:1 | | Some cracking, tactile, good adhesion | ND |
| Polyaniline camphor sulfonate (Pani-CSA)[4] | | | | | 1:1 | Crack-free, uniform, well adhered | 2.4 |
| Polyaniline camphor sulfonate (Pani-CSA)[4] | | | | | 4:1 | Crack-free, uniform, well adhered (slightly tacky) | 6.8 |
| Polyaniline formate (Pani-FA)[5] | | | 1:2.6 | | | Crack-free, uniform, well adhered (slightly tacky) | ND |
| Polyaniline dinonylnapthyl sulfonate (Pani-dNNSA)[6] | | | 1:40 | | | Badly cracked, peels readily, flakes off | ND |

[1]Trial Prod. Al 4071 (Bayer Corporation), 1.3% in $H_2O$
[2]AquaPASS 01X (Mitsubishi Rayon), 10% in $H_2O$
[3]Prepared as a 1% solution in xylene
[4]Prepared as a 1% solution in m-cresol
[5]Prepared as a 1% solution in formic acid
[6]Product 5866243 (Monsanto). Weight composition unknown-assumed ~1%.

TABLE 3

GLU Response Factors for Sol-Gel Sensors

| Conductive Polymer | Siloxane (unbuffered) | Sol-Gel Film Additive | Enzyme | Response Factor*, % per ppt |
| --- | --- | --- | --- | --- |
| PEDOT-PSSA | TMOS | Dimethoxy-siloxane/ ethylene oxide | Glucose Oxidase | −1.668 |
| Pani-DBSA | TMOS | Dimethoxy-siloxane/ ethylene oxide | Glucose Oxidase | 0.067 |

*The Response Factor was determined as percent conductivity change per parts per thousand (ppt) glucose from response data for 1 ppt glucose exposure.

We claim:

1. A sensor for detecting a biological and/or chemical material in air, said sensor comprising:
   (a) a dielectric substrate;
   (b) interdigitated electrodes attached to said substrate;
   (c) a film layer applied on top of said interdigitated electrodes, wherein the film layer comprises a conductive polymer and a sol-gel derived material;
   (d) indicator biomolecules within said film layer; and
   (e) an instrument to measure an electric current flowing through said interdigitated electrodes;
   wherein the conductive polymer and the indicator biomolecules are encapsulated within the sol-gel derived material and are thoroughly dispersed throughout the film layer;
   wherein the film layer directly contacts the air and the interdigitated electrodes;
   wherein the sol-gel derived material is a first sol-gel derived material, and wherein the film layer is prepared by the following steps:
   (1) forming a C-gel by encapsulating the conductive polymer in a second sol-gel derived material; and
   (2) forming the film layer by co-encapsulating the C-gel and the indicator biomolecules in the first sol-gel derived material; and
   wherein the first sol-gel derived material is different than the second sol-gel derived material.

2. The sensor of claim 1, wherein said dielectric substrate comprises glass, ceramic, and/or plastic material.

3. The sensor as claimed in claim 2, wherein said conductive polymer is selected from a group consisting of polyaniline, polythiophene, polypyrrole, poly (anilinesulfonic acid), polyaniline formate, poly (ethylenedioxythiophene)-polystyrene sulfonate, polyaniline dodecylbenzene sulfonate, polyaniline camphor sulfonate, and polyaniline dinonylnapthyl sulfonate;
   wherein the first sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane; and
   wherein the second sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane.

4. The sensor of claim 1, wherein said interdigitated electrodes are attached to said substrate by an adhesion layer.

5. The sensor of claim 4, wherein said adhesion layer comprises a material selected from a group consisting of titanium and an alloy of titanium and tungsten.

6. The sensor of claim 1, wherein said interdigitated electrodes each have a generally rectangular shape in a cross-section.

7. The sensor of claim 1, wherein said interdigitated electrodes each have a width within a range of between about 5 micrometers and about 25 micrometers.

8. The sensor of claim 1, wherein said interdigitated electrodes comprise a pair of electrodes defining a gap, wherein the gap is within a range of between about 5 micrometers and about 25 micrometers.

9. The sensor of claim 1, wherein said indicator biomolecules are selected from the group consisting of enzymes, antibodies, and deoxyribonucleic acid.

10. The sensor of claim 9, wherein said enzymes are selected from the group consisting of acetylcholineesterase and glucose oxidase.

11. The sensor as claimed in claim 9, wherein said conductive polymer is selected from a group consisting of polyaniline, polythiophene, polypyrrole, poly (anilinesulfonic acid), polyaniline formate, poly (ethylenedioxythiophene)-polystyrene sulfonate, polyaniline dodecylbenzene sulfonate, polyaniline camphor sulfonate, and polyaniline dinonylnapthyl sulfonate;

wherein the first sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane; and wherein the second sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane.

12. The sensor of claim 1, wherein said instrument to measure said electric current is comprised of a voltage source and an amperometer.

13. The sensor of claim 1, wherein said interdigitated electrodes are fabricated of material comprising gold.

14. The sensor of claim 1, wherein said conductive polymer is selected from a group consisting of polyaniline, polythiophene, polypyrrole, poly(anilinesulfonic acid), polyaniline formate, poly(ethylenedioxythiophene)-polystyrene sulfonate, polyaniline dodecylbenzene sulfonate, polyaniline camphor sulfonate, and polyaniline dinonylnapthyl sulfonate.

15. The sensor as claimed in claim 14, wherein the conductive polymer has no extractable counterions.

16. A method for detecting a biological and/or chemical material in air using the sensor claimed in claim 14, the method comprising:

(a) exposing the sensor to the chemical and/or biological material;

(b) applying an electric voltage to the interdigitated electrodes of the sensor; and (c) measuring a change in an electric current flowing through the interdigitated electrodes, wherein the change is caused by interaction of the biological and/or chemical material with the film layer of the sensor.

17. The sensor of claim 1, wherein said first sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane; and wherein the second sol-gel derived material comprises a product of gelation of a material selected from the group consisting of tetramethoxysiloxane, glycidoxypropyltrimethoxysiloxane, methyltrimethoxysilane, and n,p-styrylethyltrimethoxysiloxane.

18. The sensor of claim 1, wherein said interdigitated electrodes each have a width of about 15 micrometers.

19. The sensor of claim 1, wherein said interdigitated electrodes comprise a pair of electrodes defining a gap, wherein the gap is about 15 micrometers.

20. The sensor as claimed in claim 1, wherein the conductive polymer has no extractable counterions.

21. The sensor as claimed in claim 20, wherein said conductive polymer is selected from a group consisting of polyaniline, polythiophene, polypyrrole, poly (anilinesulfonic acid), polyaniline formate, poly (ethylenedioxythiophene)-polystyrene sulfonate, polyaniline dodecylbenzene sulfonate, polyaniline camphor sulfonate, and polyaniline dinonylnapthyl sulfonate;

wherein the first sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane; and wherein the second sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane.

22. The sensor as claimed in claim 1, wherein step (2) occurs in a buffered solution.

23. The sensor of claim 1, wherein said conductive polymer is selected from a group consisting of polyaniline, polythiophene, polypyrrole, poly(anilinesulfonic acid), polyaniline formate, poly(ethylenedioxythiophene)-polystyrene sulfonate, polyaniline dodecylbenzene sulfonate, polyaniline camphor sulfonate, and polyaniline dinonylnapthyl sulfonate;

wherein the first sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane; and wherein the second sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane.

24. A method for detecting a biological and/or chemical material in air using the sensor claimed in claim 23, the method comprising:

(a) exposing the sensor to the chemical and/or biological material;

(b) applying an electric voltage to the interdigitated electrodes of the sensor; and (c) measuring a change in an electric current flowing through the interdigitated electrodes, wherein the change is caused by interaction of the biological and/or chemical material with the film layer of the sensor.

25. A method for detecting a biological and/or chemical material in air using the sensor claimed in claim 1, the method comprising:

(a) exposing the sensor to the chemical and/or biological material;

(b) applying an electric voltage to the interdigitated electrodes of the sensor; and (c) measuring a change in an electric current flowing through the interdigitated electrodes, wherein the change is caused by interaction of the biological and/or chemical material with the film layer of the sensor.

26. The sensor as claimed in claim 1, wherein the indicator biomolecules have an intrinsic steric conformation.

27. A method for detecting a biological and/or chemical material in air comprising the steps of:
(a) disposing interdigitated electrodes on a dielectric substrate;
(b) applying a film layer on top of said interdigitated electrodes, wherein the film layer comprises a conductive polymer and a first sol-gel derived material;
(c) incorporating indicator biomolecules into said film layer; wherein the conductive polymer and the indicator biomolecules are encapsulated within the first sol-gel derived material and are thoroughly dispersed throughout the film layer; and wherein the film layer directly contacts the air and the interdigitated electrodes;
(d) applying an electric voltage to said interdigitated electrodes; and
(e) measuring a change in an electric current flowing through said interdigitated electrodes, said change being caused by interaction of said biological and/or chemical material with said film layer;
wherein the steps (b) and (c) comprise the following steps:
(1) forming a C-gel by encapsulating the conductive polymer in a second sol-gel derived material; and
(2) forming the film layer by co-encapsulating the C-gel and the indicator biomolecules in the first sol-gel derived material; and
wherein the first sol-gel derived material is different than the second sol-gel derived material.

28. The method of claim 27, wherein in said step of attaching of said interdigitated electrodes, said dielectric substrate comprises glass, ceramic, and/or plastic material.

29. The method of claim 27, wherein said interdigitated electrodes are attached to said substrate with use of an adhesion layer.

30. The method of claim 29, wherein said adhesion layer comprises a material selected from a group consisting of titanium and an alloy of titanium and tungsten.

31. The method of claim 27, wherein said interdigitated electrodes each have a generally rectangular shape in a cross-section.

32. The method of claim 27, wherein said interdigitated electrodes each have a width within a range of between about 5 micrometers and about 25 micrometers.

33. The method of claim 27, wherein said interdigitated electrodes comprise a pair of electrodes defining a gap, wherein the gap is within a range of between about 5 micrometers and about 25 micrometers.

34. The method of claim 27, wherein in said step of incorporating said indicator biomolecules into said film layer, said indicator biomolecules are selected from the group consisting of enzymes, antibodies, and deoxyribonucleic acid.

35. The method of claim 34, wherein said enzymes are selected from the group consisting of acetylcholineesterase and glucose oxidase.

36. The method of claim 27, wherein said step of applying an electric voltage to said interdigitated electrodes comprises applying to said interdigitated electrodes an amount of voltage between about 5 millivolts and about 300 millivolts.

37. The method of claim 27, wherein said interdigitated electrodes are fabricated of an electrically conductive material comprising gold.

38. The method of claim 27, wherein said conductive polymer is selected from a group consisting of polyaniline, polythiophene, polypyrrole, poly(anilinesulfonic acid), polyaniline formate, poly(ethylenedioxythiophene)-polystyrene sulfonate, polyaniline dodecylbenzene sulfonate, polyaniline camphor sulfonate, and polyaniline dinonylnapthyl sulfonate.

39. The method of claim 27, wherein said first sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane; and
wherein the second sol-gel derived material comprises a product of gelation of a material selected from the group consisting of tetramethoxysiloxane, glycidoxypropyltrimethoxysiloxane, methyltrimethoxysilane, and n,p-styrylethyltrimethoxysilane.

40. The method of claim 27, wherein said interdigitated electrodes each have a width of about 15 micrometers.

41. The method of claim 27, wherein said interdigitated electrodes comprise a pair of electrodes defining a gap, wherein the gap is about 15 micrometers.

42. The method of claim 27, wherein said step of applying an electric voltage to said interdigitated electrodes comprises applying to said interdigitated electrodes an amount of voltage between about 10 millivolts and about 50 millivolts.

43. A sensor for detecting a biological and/or chemical material in air, said sensor comprising:
(a) a dielectric substrate;
(b) interdigitated electrodes attached to said substrate;
(c) a film layer applied on top of said interdigitated electrodes, wherein the film layer comprises a conductive polymer and a sol-gel derived material;
(d) indicator biomolecules within said film layer; and
(e) an instrument to measure an electric current flowing through said interdigitated electrodes;
wherein the conductive polymer and the indicator biomolecules are encapsulated within the sol-gel derived material and are thoroughly dispersed throughout the film layer;
wherein the film layer directly contacts the air and the interdigitated electrodes;
wherein the sol-gel derived material is a first sol-gel derived material, and wherein the film layer is prepared by the following steps:
(1) forming an E-gel by encapsulating the indicator biomolecules in a second sol-gel derived material;
(2) forming a C-gel by encapsulating the conductive polymer in a third sol-gel derived material; and
(3) forming the film layer by co-encapsulating the E-gel and the C-gel in the first sol-gel derived material; and
wherein the second sol-gel derived material is different than the third sol-gel derived material.

44. The sensor as claimed in claim 43, wherein the conductive polymer has no extractable counterions.

45. The sensor as claimed in claim 44, wherein step (3) occurs in a buffered solution.

46. The sensor as claimed in claim 43, wherein before the film layer is formed, the C-gel is exracted to remove excess acid.

47. The sensor as claimed in claim 46, wherein step (3) occurs in a buffered solution.

48. The sensor of claim 46, wherein said conductive polymer is selected from a group consisting of polyaniline, polythiophene, polypyrrole, poly(anilinesulfonic acid), polyaniline formate, poly(ethylenedioxythiophene)-polystyrene sulfonate, polyaniline dodecylbenzene sulfonate, polyaniline camphor sulfonate, and polyaniline dinonylnapthyl sulfonate;

wherein the first sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane;

wherein the second sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane; and wherein the third sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane.

49. A method for detecting a biological and/or chemical material in air using the sensor claimed in claim 46, the method comprising:

(a) exposing the sensor to the chemical and/or biological material;

(b) applying an electric voltage to the interdigitated electrodes of the sensor; and (c) measuring a change in an electric current flowing through the interdigitated electrodes, wherein the change is caused by interaction of the biological and/or chemical material with the film layer of the sensor.

50. The method as claimed in claim 49, wherein the conductive polymer of the sensor has no extractable counterions.

51. The sensor as claimed in claim 46, wherein the conductive polymer has no extractable counterions.

52. The sensor as claimed in claim 48, wherein the conductive polymer has no extractable counterions.

53. The sensor as claimed in claim 43, wherein before the film layer is formed, the C-gel is exracted with water to remove excess acid.

54. The sensor of claim 53, wherein said conductive polymer is selected from a group consisting of polyaniline, polythiophene, polypyrrole, poly(anilinesulfonic acid), polyaniline formate, poly(ethylenedioxythiophene)-polystyrene sulfonate, polyaniline dodecylbenzene sulfonate, polyaniline camphor sulfonate, and polyaniline dinonylnapthyl sulfonate;

wherein the first sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane;

wherein the second sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane; and wherein the third sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane.

55. The sensor as claimed in claim 43, wherein step (3) occurs in a buffered solution.

56. The sensor of claim 43, wherein said conductive polymer is selected from a group consisting of polyaniline, polythiophene, polypyrrole, poly(anilinesulfonic acid), polyaniline formate, poly(ethylenedioxythiophene)-polystyrene sulfonate, polyaniline dodecylbenzene sulfonate, polyaniline camphor sulfonate, and polyaniline dinonylnapthyl sulfonate;

wherein the first sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane;

wherein the second sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane; and wherein the third sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane.

57. A method for detecting a biological and/or chemical material in air using the sensor claimed in claim 43, the method comprising:

(a) exposing the sensor to the chemical and/or biological material;

(b) applying an electric voltage to the interdigitated electrodes of the sensor; and (c) measuring a change in an electric current flowing through the interdigitated electrodes, wherein the change is caused by interaction of the biological and/or chemical material with the film layer of the sensor.

58. A sensor for detecting a biological and/or chemical material in air, said sensor comprising:

(a) a dielectric substrate;

(b) interdigitated electrodes attached to said substrate;

(c) a film layer applied on top of said interdigitated electrodes, wherein the film layer comprises a conductive polymer and a first sol-gel derived material;

(d) indicator biomolecules within said film layer; and (e) an instrument to measure an electric current flowing through said interdigitated electrodes;

wherein the film layer is prepared by the following steps:

(1) forming an E-gel by encapsulating the indicator biomolecules in a second sol-gel derived material;

(2) forming a C-gel by encapsulating the conductive polymer in a third sol-gel derived material; and (3) forming the film layer by co-encapsulating the E-gel and the C-gel in the first sol-gel derived material; and wherein the second sol-gel derived material is different, than the third sol-gel derived material.

59. The sensor as claimed in claim 58, wherein the conductive polymer has no extractable counterions.

60. The sensor as claimed in claim 59, wherein said conductive polymer is selected from a group consisting of polyaniline, polythiophene, polypyrrole, poly (anilinesulfonic acid), polyaniline formate, poly(ethylenedioxythiophene)-polystyrene sulfonate, polyaniline dodecylbenzene sulfonate, polyaniline camphor sulfonate, and polyaniline dinonylnapthyl sulfonate;

wherein the first sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane;

wherein the second sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane; and wherein the third sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane.

61. The sensor as claimed in claim 58, wherein before the film layer is formed, the C-gel is exracted to remove excess acid.

62. The sensor as claimed in claim 58, wherein before the film layer is formed, the C-gel is exracted with water to remove excess acid.

63. The sensor as claimed in claim 58, wherein step (3) occurs in a buffered solution.

64. The sensor of claim 58, wherein said conductive polymer is selected from a group consisting of polyaniline, polythiophene, polypyrrole, poly(anilinesulfonic acid), polyaniline formate, poly(ethylenedioxythiophene)-polystyrene sulfonate, polyaniline dodecylbenzene sulfonate, polyaniline camphor sulfonate, and polyaniline dinonylnapthyl sulfonate;

wherein the first sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane;

wherein the second sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane; and wherein the third sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane.

65. The sensor as claimed in claim 64, wherein said dielectric substrate comprises glass, ceramic, and/or plastic material; and wherein said indicator biomolecules are selected from the group consisting of enzymes, antibodies, and deoxyribonucleic acid.

66. A method for detecting a biological and/or chemical material in air using the sensor claimed in claim 58, the method comprising:
(a) exposing the sensor to the chemical and/or biological material;
(b) applying an electric voltage to the interdigitated electrodes of the sensor; and
(c) measuring a change in an electric current flowing through the interdigitated electrodes, wherein the change is caused by interaction of the biological and/or chemical material with the film layer of the sensor.

67. A sensor for detecting a biological and/or chemical material in air, said sensor comprising:
(a) a dielectric substrate;
(b) interdigitated electrodes attached to said substrate;
(c) a film layer applied on top of said interdigitated electrodes, wherein the film layer comprises a conductive polymer and a first sol-gel derived material;
(d) indicator biomolecules within said film layer; and
(e) an instrument to measure an electric current flowing through said interdigitated electrodes;
wherein the film layer is prepared by the following steps:
(1) forming a C-gel by encapsulating the conductive polymer in a second sol-gel derived material; and
(2) forming the film layer by co-encapsulating the C-gel and the indicator biomolecules in the first sol-gel derived material; and
wherein the first sol-gel derived material is different than the second sol-gel derived material.

68. The sensor as claimed in claim 67, wherein the conductive polymer has no extractable counterions.

69. The sensor as claimed in claim 68, wherein said conductive polymer is selected from a group consisting of polyaniline, polythiophene, polypyrrole, poly(anilinesulfonic acid), polyaniline formate, poly(ethylenedioxythiophene)-polystyrene slulfonate, polyaniline dodecylbenzene sulfonate, polyaniline camphor sulfonate, and polyaniline dinonylnapthyl sulfonate;

wherein the first sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane; and wherein the second sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane.

70. The sensor as claimed in claim 67, wherein step (2) occurs in a buffered solution.

71. The sensor of claim 67, wherein said conductive polymer is selected from a group consisting of polyaniline, polythiophene, polypyrrole, poly (anilinesulfonic acid), polyaniline formate, poly(ethylenedioxythiophene)-polystyrene sulfonate, polyaniline dodecylbenzene sulfonate, polyaniline camphor sulfonate, and polyaniline dinonylnapthyl sulfonate;

wherein the first sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane; and wherein the second sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane.

72. The sensor as claimed in claim 71, wherein said dielectric substrate comprises glass, ceramic, and/or plastic material; and wherein said indicator biomolecules are selected from the group consisting of enzymes, antibodies, and deoxyribonucleic acid.

73. A method for detecting a biological and/or chemical material in air using the sensor claimed in claim 67, the method comprising:
  (a) exposing the sensor to the chemical and/or biological material;
  (b) applying an electric voltage to the interdigitated electrodes of the sensor; and
  (c) measuring a change in an electric current flowing through the interdigitated electrodes, wherein the change is caused by interaction of the biological and/or chemical material with the film layer of the sensor.

74. A method for making a sensor for detecting a biological and/or chemical material in air, the method comprising:
  (1) providing a dielectric substrate with interdigitated electrodes attached to the substrate; and
  (2) applying a film layer on top of the interdigitated electrodes;
  wherein the film layer comprises a conductive polymer, indicator biomolecules, and a first sol-gel derived material; wherein the conductive polymer and the indicator biomolecules are encapsulated within the first sol-gel derived material;
  wherein the film layer in step (2) is formed by the following steps:
    (a) forming an E-gel by encapsulating the indicator biomolecules in a second sol-gel derived material;
    (b) forming a C-gel by encapsulating the conductive polymer in a third sol-gel derived material; and
    (c) forming the film layer by co-encapsulating the E-gel and the C-gel in the first sol-gel derived material; and
  wherein the second sol-gel derived material is different than the third sol-gel derived material.

75. The method for making a sensor as claimed in claim 74, wherein the conductive polymer has no extractable counterions.

76. The method for making a sensor as claimed in claim 74, wherein before the film layer is formed, the C-gel is exracted to remove excess acid.

77. The method for making a sensor as claimed in claim 74, wherein step (c) occurs in a buffered solution.

78. The method for making a sensor as claimed in claim 74, wherein the conductive polymer is selected from a group consisting of polyaniline, polythiophene, polypyrrole, poly(anilinesulfonic acid), polyaniline formate, poly(ethylenedioxythiophene)-polystyrene sulfonate, polyaniline dodecylbenzene sulfonate, polyaniline camphor sulfonate, and polyaniline dinonylnapthyl sulfonate;
  wherein the first sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane;
  wherein the second sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane; and
  wherein the third sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane.

79. A method for making a sensor for detecting a biological and/or chemical material in air, the method comprising:
  (1) providing a dielectric substrate with interdigitated electrodes attached to the substrate; and
  (2) applying a film layer on top of the interdigitated electrodes;
  wherein the film layer comprises a conductive polymer, indicator biomolecules, and a first sol-gel derived material; wherein the conductive polymer and the indicator biomolecules are encapsulated within the first sol-gel derived material; and
  wherein the film layer in step (2) is formed by the following steps:
    (a) forming a C-gel by encapsulating the conductive polymer in a second sol-gel derived material; and
    (b) forming the film layer by co-encapsulating the C-gel and the indicator biomolecules in the first sol-gel derived material; and
  wherein the first sol-gel derived material is different than the second sol-gel derived material.

80. The method for making a sensor as claimed in claim 79, wherein the conductive polymer has no extractable counterions.

81. The method for making a sensor as claimed in claim 79, wherein before the film layer is formed, the C-gel is exracted with water to remove excess acid.

82. The method for making a sensor as claimed in claim 79, wherein step (b) occurs in a buffered solution.

83. The method for making a sensor as claimed in claim 79, wherein the conductive polymer is selected from a group consisting of polyaniline, polythiophene, polypyrrole, poly(anilinesulfonic acid), polyaniline formate, poly(ethylenedioxythiophene)-polystyrene sulfonate, polyaniline dodecylbenzene sulfonate, polyaniline camphor sulfonate, and polyaniline dinonylnapthyl sulfonate;
  wherein the first sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane; and
  wherein the second sol-gel derived material comprises a product of gelation of a material selected from a group consisting of tetramethoxysiloxane, glycidoxypropyltrimethoxysiloxane, methyltrimethoxysilane, and n,p-styrylethyltrimethoxysiloxane.

* * * * *